United States Patent
Landau et al.

(12) 
(10) Patent No.: US 6,383,168 B1
(45) Date of Patent: *May 7, 2002

(54) NEEDLELESS SYRINGE WITH PREFILLED CARTRIDGE

(75) Inventors: Sergio Landau, Laguna Niguel, CA (US); James M. Bonicatto, Portland, OR (US)

(73) Assignee: Bioject Medical Technologies Inc., Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/539,731

(22) Filed: Mar. 30, 2000

Related U.S. Application Data

(63) Continuation-in-part of application No. 09/207,398, filed on Dec. 8, 1998, now Pat. No. 6,132,395.

(51) Int. Cl.[7] .................................................. A61M 5/30
(52) U.S. Cl. ...................... 604/268; 604/236; 604/238; 604/249
(58) Field of Search ........................ 604/236, 68, 238, 604/249, 118, 131, 121, 140, 141, 146, 156, 218, 231, 232, 264

(56) References Cited

U.S. PATENT DOCUMENTS

| | | |
|---|---|---|
| 3,729,031 A | 4/1973 | Baldwin |
| 3,940,003 A | 2/1976 | Larson |
| 3,941,128 A | 3/1976 | Baldwin |
| 4,592,745 A | 6/1986 | Rex et al. |
| 4,662,878 A | 5/1987 | Lindmayer |
| 4,713,061 A | 12/1987 | Tarello et al. |
| 4,747,839 A | 5/1988 | Tarello et al. |
| 4,790,824 A | 12/1988 | Morrow et al. |
| 4,850,967 A | 7/1989 | Cosmai |
| 4,886,495 A | 12/1989 | Reynolds |
| 4,909,794 A | 3/1990 | Haber et al. |
| 4,940,460 A | 7/1990 | Casey et al. |
| 4,941,880 A | 7/1990 | Burns |
| 5,024,656 A | 6/1991 | Gasaway et al. |
| 5,135,514 A | 8/1992 | Kimber |
| 5,273,544 A | 12/1993 | Van der Wal |
| 5,364,386 A | 11/1994 | Fukuoka et al. |
| 5,399,163 A | 3/1995 | Peterson et al. |
| 5,462,535 A | 10/1995 | Bonnichsen et al. |
| 5,472,022 A | 12/1995 | Michel et al. |
| 5,573,513 A | 11/1996 | Wozencroft |
| 5,716,348 A | 2/1998 | Marinacci et al. |

FOREIGN PATENT DOCUMENTS

WO  PCT/GB97/00812   3/1997

*Primary Examiner*—Sharon Kennedy
*Assistant Examiner*—Kevin C. Sirmons
(74) *Attorney, Agent, or Firm*—Kolisch Hartwell Dickinson McCormack & Heuser

(57) ABSTRACT

In accordance with an embodiment of the invention, a needleless injection apparatus includes a cartridge having a plunger disposed at a rearward end. The cartridge includes an inner portion with a throat at a forward portion and a displaceable outlet valve initially disposed within the cartridge throat. The cartridge further includes a generally outwardly facing surface and a system for selectively providing driving force to drive the plunger in a forward direction. The apparatus also includes a nozzle for receiving the cartridge, the nozzle defining a rearward, cartridge-receiving portion, and having a forward portion terminating in and defining a valve abutment surface with a plurality of channels and an injection orifice. The forward portion of the nozzle being configured to receive the valve when the valve is displaced to a forwardly disposed position such that the valve is disposed against the valve abutment surface, and so that the inner portion of the cartridge has fluid access to the orifice via the channels. The nozzle further includes a generally inwardly facing surface that abuts the cartridge surface, and a seal disposed between the outwardly facing surface of the cartridge and the inwardly facing surface of the nozzle for at least reducing leakage of injectate therebetween.

18 Claims, 11 Drawing Sheets

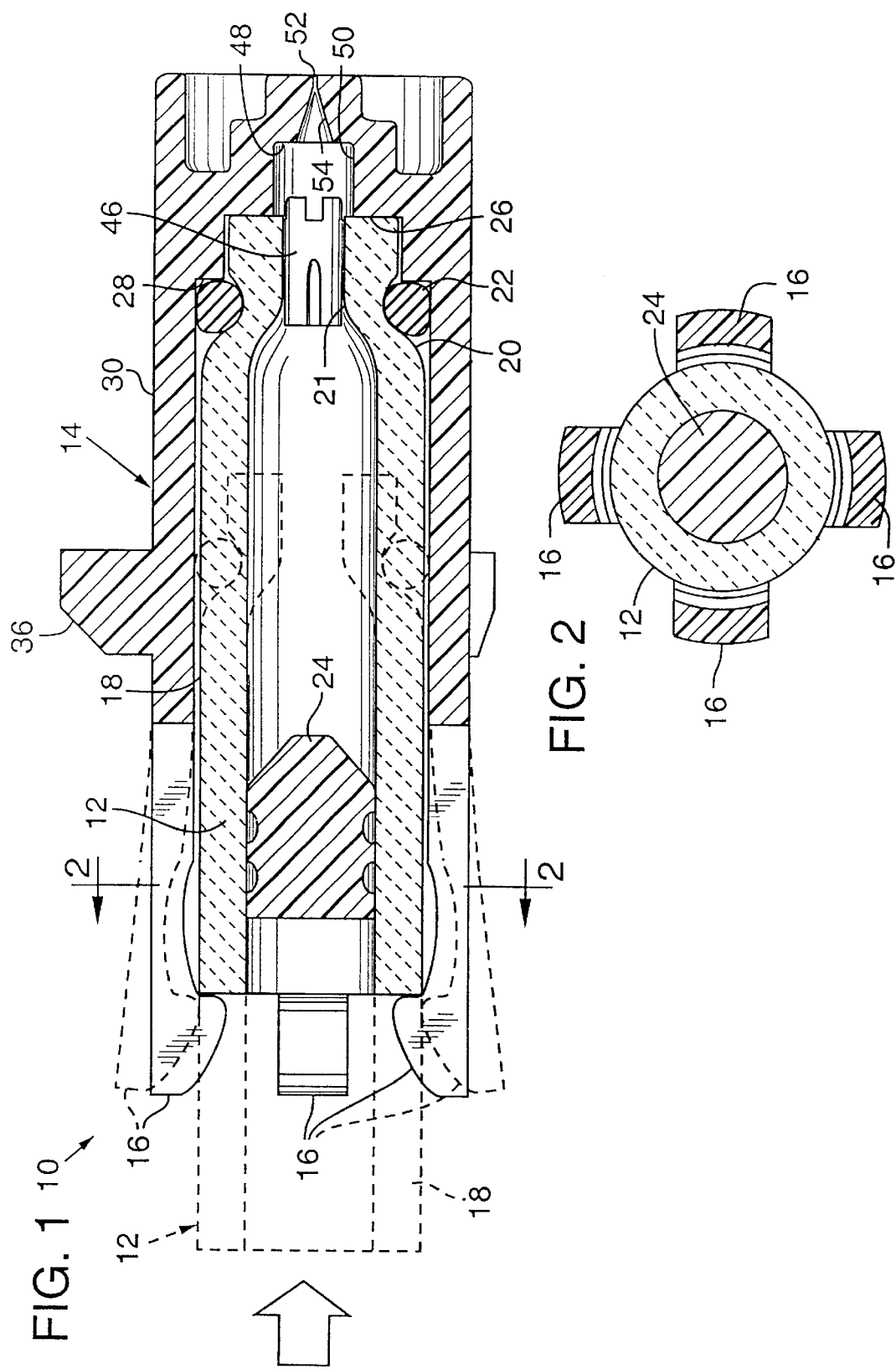

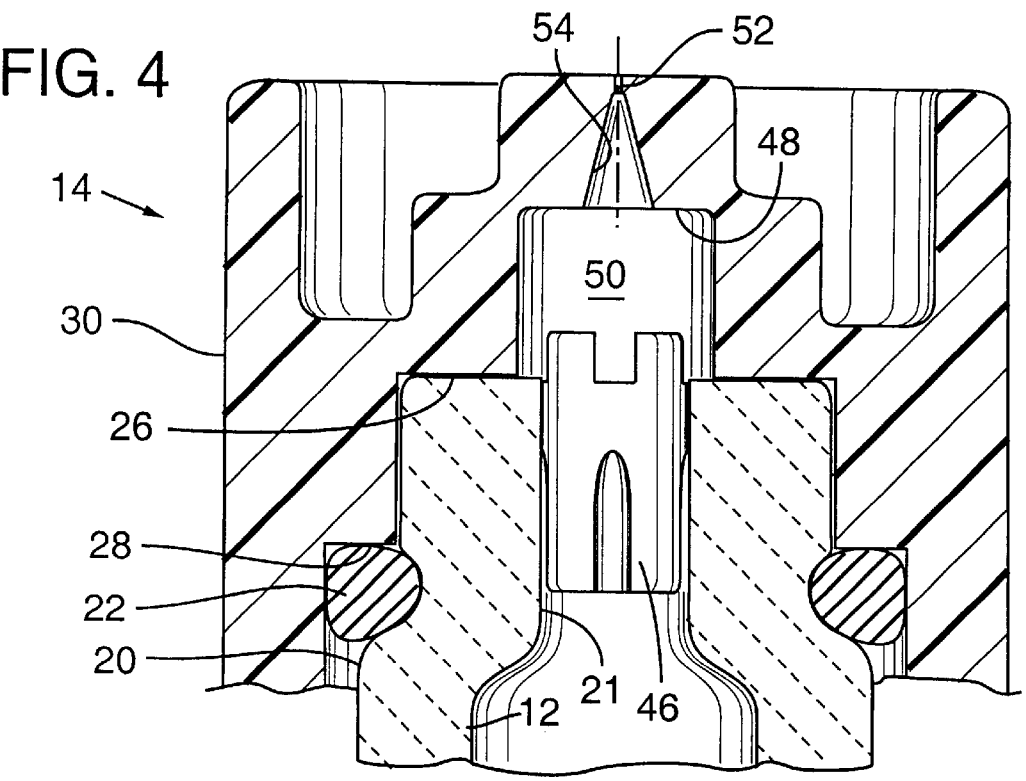
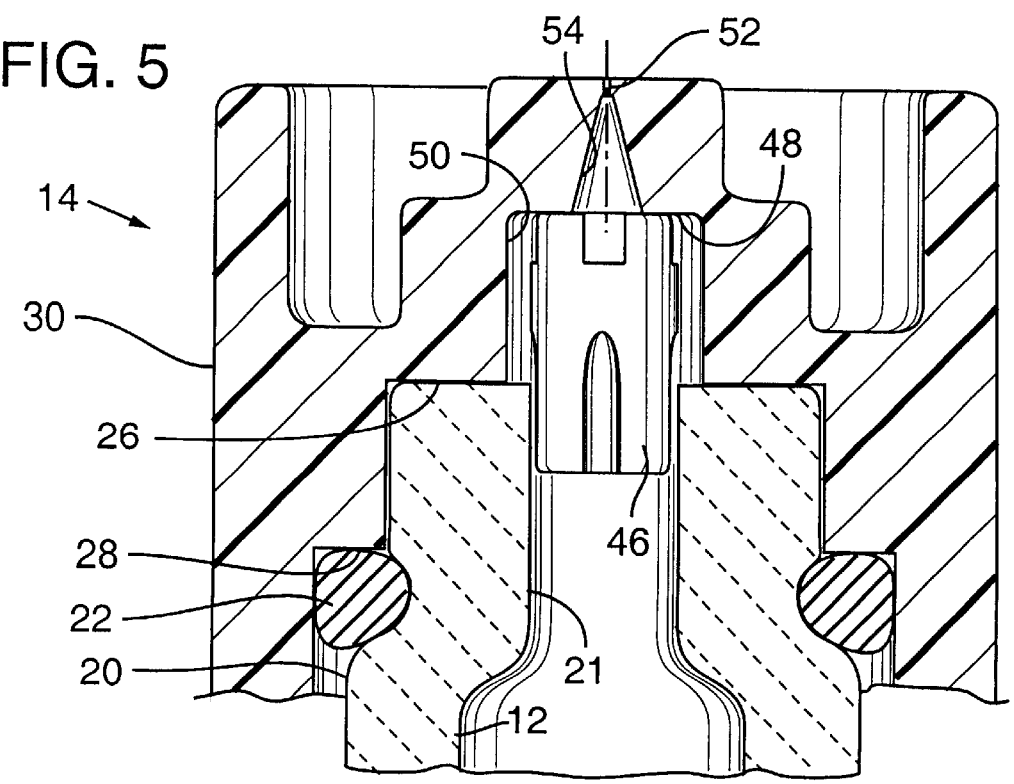

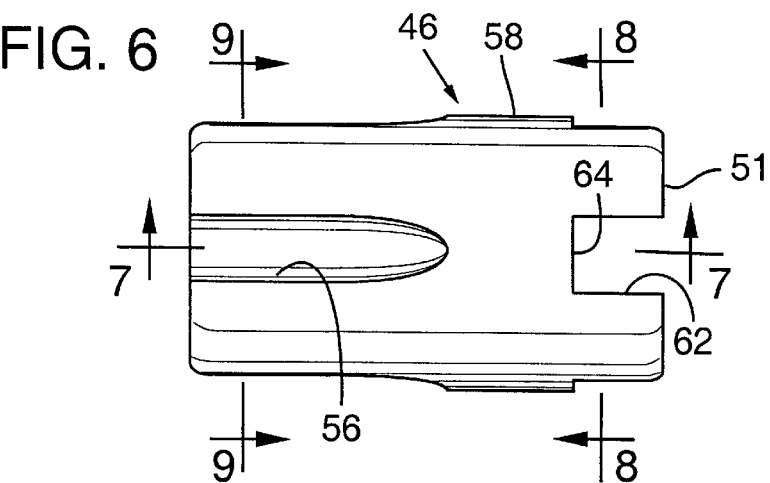
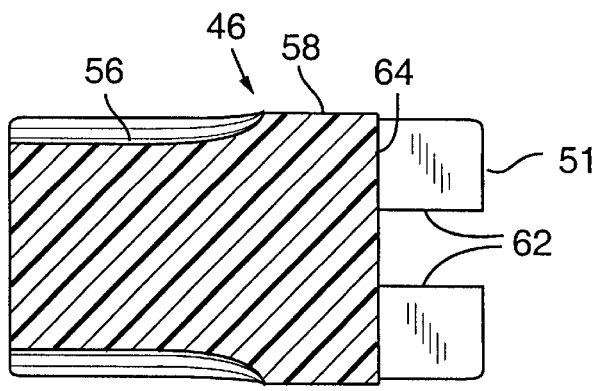
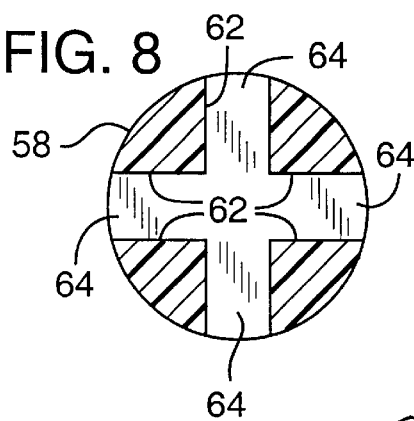
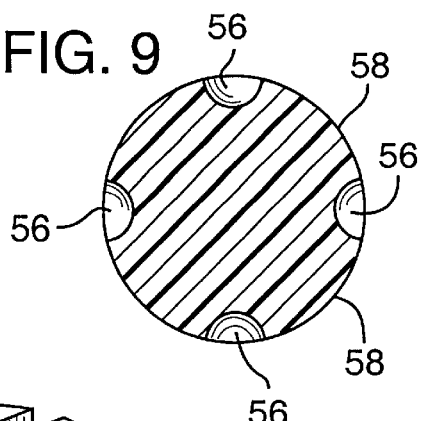
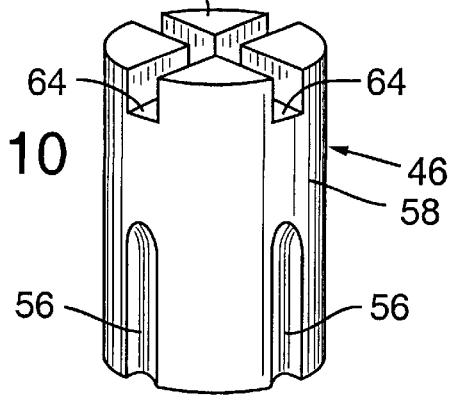

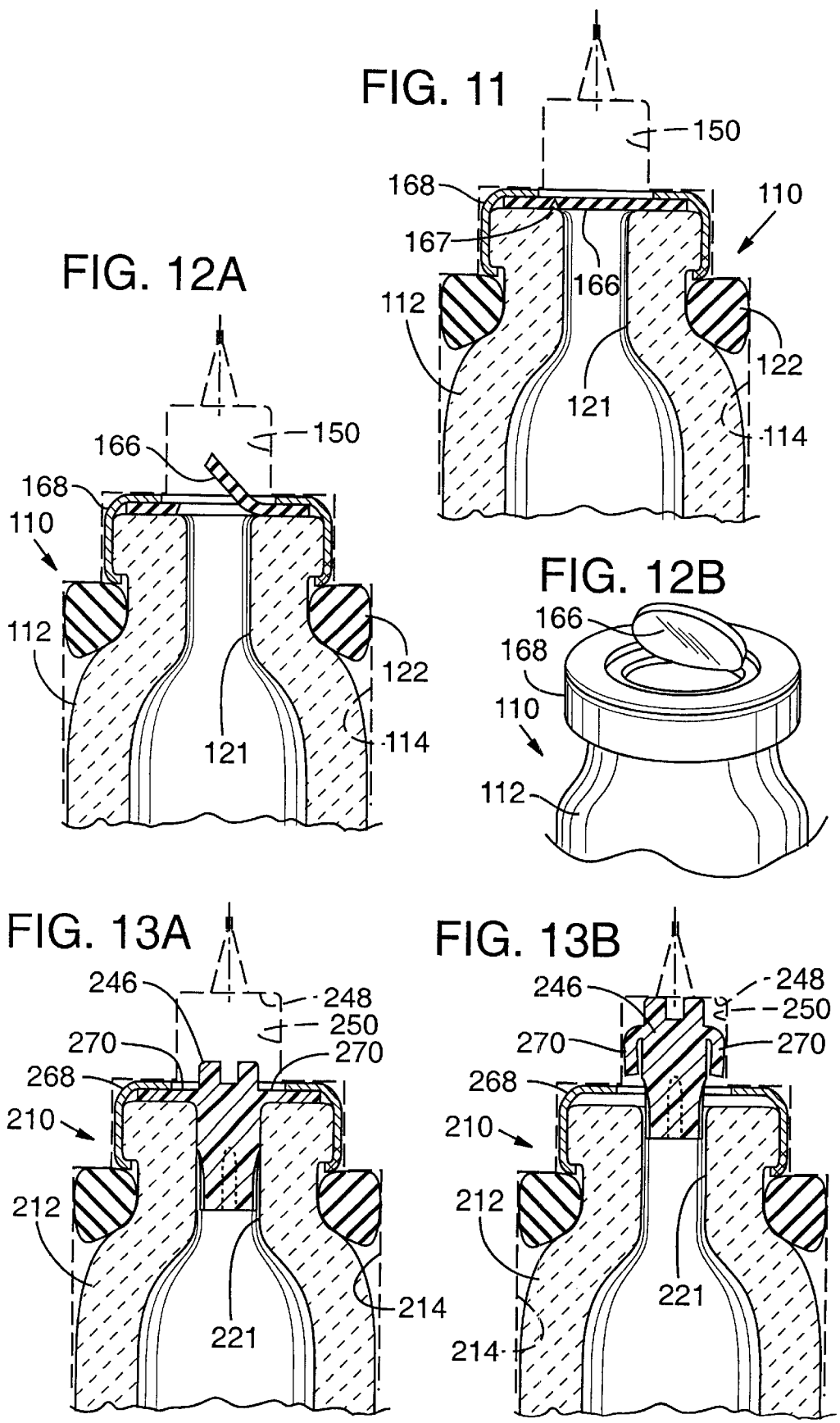

US 6,383,168 B1

NEEDLELESS SYRINGE WITH PREFILLED CARTRIDGE

This application is a continuation-in-part of Ser. No. 09/207,398, filed Dec. 8, 1998, now U.S. Pat. No. 6,132,395. This invention relates to a needleless injection system which includes a prefilled cartridge.

BACKGROUND OF THE INVENTION

One of the problems inherently present in the packaging of liquid parenteral drugs is that there is not enough biocompatibility data about the interaction between those drugs and thermoplastic containers. While plastic is commonly used in many injection devices, most parenteral drugs cannot be exposed to most plastics other than for a short period immediately prior to the injection. This is because the drug or injectate may chemically react with the plastic, or cause materials in the plastic to leach into the injectate, thereby introducing impurities in the drug. In periods of extended storage, such exposure to a plastic container may result in degradation of the drug. For these reasons, the pharmaceutical industry normally avoids the storage of injectate in some thermoplastic materials such as polypropylene, which is commonly used in syringes and related injection paraphernalia. Similarly, there is no long term biocompatibility data on engineering or high strength thermoplastics, such as polycarbonate, which is the plastic most commonly used in needleless injection systems.

For this reason, injectates are typically stored in glass vials. Immediately prior to injection, the injectate chamber of a needleless injection system is filled from a glass vial containing the drug. This normally requires the use of a vial adapter, sometimes referred to as a blunt fill device, or an access needle which pierces the protective membrane over the top of the vial and then directs injectate down into the chamber or cartridge of the needleless injection system.

There are a number of drawbacks with this conventional approach. For example, the extra step of having to transfer the drug from the glass vial to the needleless injection system is time consuming and can be troublesome to a patient who is trying to administer the drug at home and who may have physical infirmities. Even for those who are not infirm, an adapter must be on-hand, and it must be sterile to prevent contamination of the injectate. The adapter typically includes a transfer needle with a sharp point at one end to pierce the vial membrane, and that can lead to injury, to unintended introduction of the injectate into the handling personnel or administrator, and/or to contamination of the injectate. This extra step of filling the needleless injection system immediately prior to injection also brings about the possibility of leakage and waste of injectate and, if improperly performed, can introduce air into the injection system. The introduction of air presents difficulties in a needleless injection system, because unlike a conventional needle and syringe system, it is not easy to bleed air out of the chamber of a needleless device. Therefore, firing the injection system with a portion of its chamber filled with air results in a lower dosage being injected into the patient. It is also possible that the injection may take place at an improper pressure. One advantage of the needleless injection systems of Bioject, Inc., assignee of this patent, is that they are able to inject a precisely predetermined amount of injectate at a predetermined, precise location in the tissue of the patient. The introduction of air may make it difficult to achieve such precision.

Accordingly, it is an object of the present invention to provide for the prefilling of a cartridge to be used in a needleless injection system.

SUMMARY OF THE INVENTION

The invention provides a cartridge and nozzle assembly having a nozzle with a valve-receiving portion including a plurality of channels to facilitate flow of injectate to the nozzle orifice. Specifically, the assembly includes a cartridge having a plunger disposed at a rearward end thereof, with an inner portion having a throat at a forward portion thereof, the cartridge further including a generally laterally extending interface surface. Also included is a displaceable outlet valve initially disposed within the throat, the outlet valve having a channel-less valve body. The nozzle receives the cartridge in a rearwardly-directed cartridge-receiving portion, and includes a forward portion defining a valve-receiving portion with a plurality of channels and an injection orifice. Thus, the inner portion of the cartridge has fluid access to the orifice via the channels. The nozzle also includes a generally extending interface surface which abuts the cartridge interface surface. Finally, a seal is disposed between the cartridge and the nozzle rearward of the interface surfaces for preventing or at least reducing leakage of injectate therebetween.

Another aspect of the invention provides a method for preparing a needleless injection system. The method includes the following steps, not necessarily in the order recited: (1) selecting a glass cartridge with a plunger positionable at a rearward end and an inner portion with a throat at a forward portion, and an outlet valve positionable within the throat, the cartridge further including a generally laterally extending interface surface; (2) positioning a seal on the cartridge rearward of the laterally extending interface surface; (3) positioning one of the plunger or the outlet valve within the cartridge; (4) filling the cartridge with injectate prior to positioning the other of the plunger or the outlet valve in the cartridge; (5) positioning the other of the plunger or the outlet valve within the cartridge; (6) selecting a nozzle which includes a rearward, cartridge-receiving portion and a forward portion defining a valve-receiving portion with a plurality of channels and an injection orifice defined therein, the forward portion being configured to receive the valve when the valve is displaced to a forwardly disposed position, the nozzle further including a generally laterally extending interface surface; (7) installing the cartridge into the nozzle to form a cartridge/seal assembly such that the interface surfaces are in abutment and the seal is disposed rearwardly of such abutment; and (8) maintaining the cartridge/seal assembly in a sterile environment prior to use.

An additional aspect of this method includes the step of mounting the cartridge/nozzle assembly to the front end of an injector by exerting rearward pressure on the assembly such that an injector ram exerts forward pressure on the plunger, causing the outlet valve to be displaced from the throat and into the valve-receiving portion and resulting in the injectate displacing air in the forward portion of the nozzle.

With this last-recited aspect, injection can be affected by activating the injector, causing the injector ram to push forwardly on the plunger, causing injectate to be driven out of the nozzle orifice.

BRIEF DESCRIPTION OF THE DRAWINGS

FIG. 1 is a side elevation sectional view of the prefilled cartridge of the present invention, with its initial position prior to insertion of the cartridge shown in phantom, and the inserted position, prior to initial pressurization, shown in solid lines;

FIG. 2 is an end elevation sectional view taken along line 2—2 of FIG. 1, showing the cartridge in its inserted position;

FIG. 4 is an enlarged, fragmentary, side elevation sectional view of the outlet valve and adjacent portions of the cartridge/nozzle assembly of the embodiment of FIG. 1, with the outlet valve shown in its unpressurized position;

FIG. 5 is a view corresponding to FIG. 4 except that the outlet valve is shown in section and is shifted to its forward position;

FIG. 6 is an enlarged side elevation view of the outlet valve of the embodiment of FIG. 1;

FIG. 7 is a side elevation sectional view taken along line 7—7 of FIG. 6;

FIG. 8 is an end elevation sectional view taken along line 8—8 of FIG. 6 showing the forward portion of the outlet valve;

FIG. 9 is an end elevation sectional view taken along line 9—9 of FIG. 4 showing the rearward portion of the outlet valve;

FIG. 10 is an isometric view of the outlet valve of FIGS. 1–9;

FIG. 11 is a side elevation sectional view of an alternate embodiment showing a membrane in place of the outlet valve;

FIG. 12A is a side elevation view of the embodiment of FIG. 11, with the membrane broken;

FIG. 12B is an isometric view corresponding to FIG. 12A;

FIG. 13A is a side elevation sectional view of a second alternate embodiment, with the outlet valve in its closed position;

FIG. 13B is a view corresponding to FIG. 13A except that the outlet valve is shown in its forward position;

DETAILED DESCRIPTION OF THE PREFERRED EMBODIMENTS

The Embodiment of FIGS. 1–10

Figure 3:
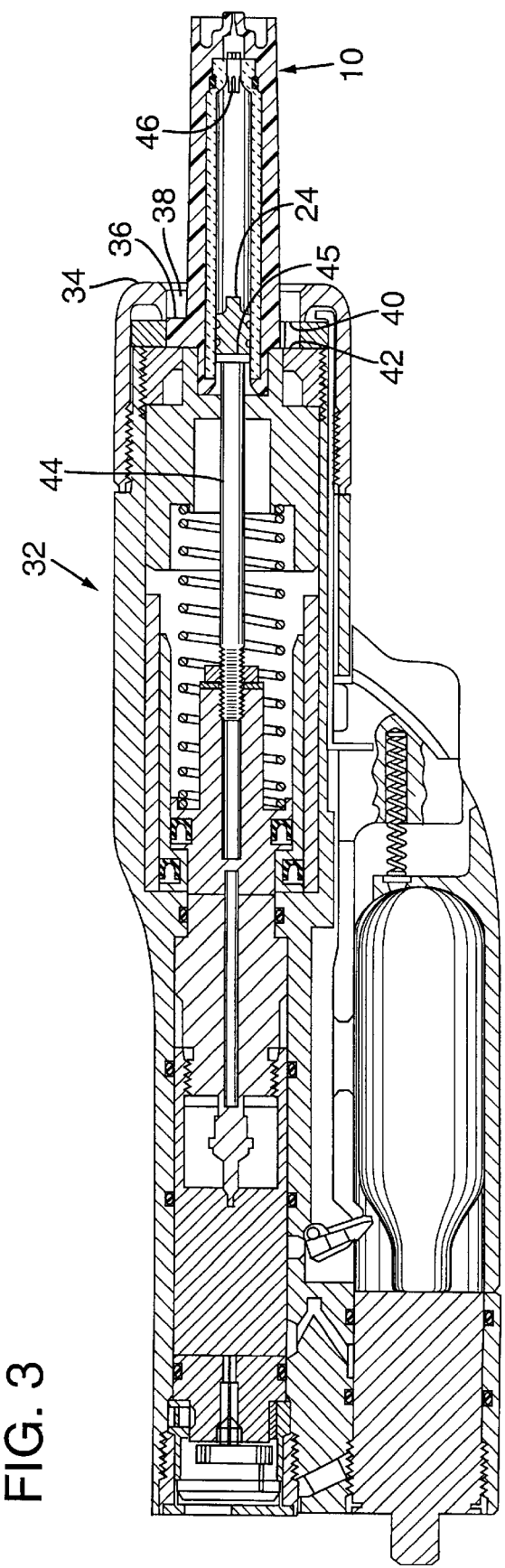
FIG. 3 is a side elevation sectional view showing the position of the cartridge and nozzle within a preferred embodiment of the needleless injection system.

The objects of the invention are best achieved when the invention takes the form of the embodiment depicted in FIGS. 1–10. This description will initially make reference to those figures. Depicted generally at 10 is a cartridge/nozzle assembly in which the cartridge may be prefilled with liquid injectate. The assembly includes a cartridge 12 which, in the preferred embodiment, is formed of strengthened glass, and a nozzle 14, which, in the preferred embodiment, is fabricated of high strength thermoplastic, typically polycarbonate. The nozzle 14 is of conventional design except the rearward (or leftward in FIG. 1) portion includes a plurality of evenly spaced tangs 16. In the depicted embodiment, four such tangs are included, positioned at 90-degree intervals around the nozzle, two of which are shown in phantom in FIG. 1. Alternatively, three or even two such tangs may be utilized.

With the cartridge 12 disposed in its partially inserted position depicted in phantom in FIG. 1, tangs 16 are displaced radially outwardly and are held there by cartridge walls 18. It is easy to insert cartridge 12 into this partially installed position because the walls 18 of the cartridge taper at 20 at the forward end thereof. Tapered walls 20 thereby define an inner throat 21 disposed in the forward end of cartridge 12. An O-ring 22 is typically disposed adjacent this forward, tapered end of cartridge 12 between the cartridge and nozzle 14. A step 28 is included in the inner surface of side walls 30 of nozzle 14 to provide a stop and a sealing surface for O-ring 22 disposed between the tapered portion 20 of cartridge walls 18 and the inner surface of nozzle side walls 30. The O-ring thus prevents the flow of injectate along the interface between the outer surface of cartridge walls 18 and the inner surface of nozzle side walls 30. A plunger 24 is disposed within walls 18 of cartridge 12, and controls the injection of injectate out of the cartridge, as desired by the operator. At the factory, or at the user's location, cartridge 12 is inserted into nozzle 14, as shown in FIG. 1, and is then pressed forwardly and entirely into the nozzle, as shown in solid lines in FIG. 1, until the tapered portion 20 of walls 18 of cartridge 12 abut a cartridge abutment face 26 in the forward end of nozzle 14.

One advantage of the present invention is that it permits cartridge 12 to be prefilled with injectate and then stored at a suitable location, whether that be at the factory, at a hospital or other medical facility, a pharmacy, in an ambulance, or at the residence of a patient who may need the medication. Alternatively, cartridge 12 may be prefilled and stored in position within nozzle 14, ready to be inserted into a needleless injector, such as that shown generally at 32 in FIG. 3.

The needleless injector 32 with which the cartridge/nozzle assembly 10 is typically used is depicted in Peterson et al. U.S. Pat. No. 5,399,163, although the assembly 10 may be used in a wide variety of other needleless injection systems. The Peterson '163 patent is incorporated herein by reference. As shown in FIG. 3, the cartridge/nozzle assembly 10 is mounted to the front end 34 of injector 32 by a series of evenly spaced lugs 36, three of which are typically disposed at 120-degree intervals around the periphery of nozzle 14. The lugs 36 in nozzle 14 are aligned to pass through corresponding spaces 38 disposed in the front end 34 of injector 32. The cartridge/nozzle assembly 10 is then rotated to lock it in position such that lugs 36 are disposed between the inner surface 40 of front end 34 of injector 32 and a lug abutment surface 42 in injector 32. As the cartridge nozzle assembly 10 is inserted into injector 32, the forward end of a ram 44 abuts a somewhat resilient Teflon pad 45 mounted to the rearward end of the plunger 24. Contact between ram 44, pad 45 and plunger 24 is made prior to lugs 36 reaching lug abutment surface 42 in injector 32. As cartridge 12 is continued to be pushed into injector 32, with lugs 36 disposed against lug abutment surface 42, the ram 44, which is stationary, will cause plunger 24 to slide forward, which in consequence, will cause liquid injectate inside cartridge 12 to move outlet valve 46 forward, allowing flow of liquid into a recessed portion 50 and toward the jet orifice 52 (see FIG. 1). The amount of liquid flowing through outlet valve 46 during the insertion of cartridge 12 in injector 32 is controlled by the length of ram 44 relative to the lug abutment surface 42.

As shown best in FIG. 4, an outlet valve 46 is disposed adjacent the inner surface of tapered walls 21 in the forward end of cartridge 12. This valve 46 is typically fabricated of butyl rubber or another resilient material which is capable of being sterilized prior to insertion into cartridge 12. As shown in FIG. 4, valve 46 is designed to fit tightly within the forward end of cartridge 12. As best shown in FIGS. 6–10, the mid-portion or body 58 of outlet valve 46 is normally round in cross-section, and is sized such that it fits snugly within the tapered walls 20 of cartridge 12. The rearward portion of outlet valve 46 includes four rounded slots 56 which extend rearwardly from a centrally disposed body portion 58 of outlet valve 46. The forward end 51 of outlet valve 46 includes forwardly extending members 62 which extend axially from body 58 of outlet valve 46 to define two perpendicular valve channels 64.

In the preferred embodiment, the outer diameter of the outlet valve is slightly greater than the inner diameter of tapered walls 21, with the outlet valve outer diameter being typically 0.105 inch, and the inner diameter of the taper walls being 0.098 inch. This difference in sizing, along with the somewhat elastic properties of PTFE (polytetrafluoroethylene) or other material from which outlet valve 46 is formed, permits a friction fit in the front end of cartridge 12. However, once hydraulic pressure is exerted on outlet valve 46, such as when the cartridge/nozzle assembly 10 is pushed into place in needleless injector 32 while ram 44 is held stationary within the injector, outlet valve 46 is forced to a forward, initially-pressurized position depicted in FIG. 5, with the forward end of outlet valve 46 disposed against valve abutment surface 48 at the forward end of recessed portion 50 of the forward end of nozzle 14. This abutment surface 48 typically includes a surface or shoulder extending in a direction perpendicular to the longitudinal dimension of nozzle 14 and to the direction of displacement of outlet valve 46. The forward end 51 of outlet valve 46 typically includes a surface which complements that of the abutment surface shoulder, also extending perpendicular to the longitudinal dimension of the valve and to the direction of displacement of the valve. The forward end of recessed portion 50 terminates in a jet orifice 52 having a generally conical-shaped orifice channel 54. The relative sizing of the respective outlet valve 46, the inner surface of tapered walls 20, and recessed portion 50 are such that fluid is permitted to flow from the cartridge and into the recessed portion surrounding the outlet valve and perhaps even out of injection aperture 52.

Operation of the Embodiment of FIGS. 1–10

In operation, at the factory or at the user's location, cartridge 12 is inserted into nozzle 14 as shown in phantom in FIG. 1, and is then pressed forwardly and entirely into the nozzle, as shown in solid lines in FIG. 1 until the tapered portion 20 of walls 18 of cartridge 12 abut cartridge abutment face 26 in the forward end of nozzle 14. Prior to the mounting of the cartridge/nozzle assembly 10 within injector 32, as shown in FIGS. 1 and 4, outlet valve 46 is lodged in the throat 21 of cartridge 12 in its pre-initial pressure position. With the valve in this position, fluid disposed within the cartridge is prevented from flowing out of the throat 21 by the body portion 58 of valve 46.

Because ram 44 in injector 32 is held stationary, as the cartridge/nozzle assembly 10 is inserted into an injector 32, the pressure of plunger 24 against the fluid disposed in cartridge 12 causes outlet valve 46 to shift into its forward initially pressurized position shown in FIG. 5. Because outlet valve 46 includes slots 56, fluid within the cartridge is permitted to flow through cartridge throat 21 and into cartridge recessed portion 50. Forward valve channels 64 in outlet valve 46 permit the fluid rushing into recessed portion 50 to displace any air in the recessed portion, forcing that air out orifice channel 54 and orifice 52, so that the recessed portion, the orifice channel, and the aperture are all entirely filled with injectate. This may also result in some injectate dribbling out the jet orifice, but because it is an insignificant amount, it is of little concern. What is important is that all of the air is displaced from the front of nozzle 14. This permits the amount of injectate which will be injected into the patient to be precisely measured, which would not be possible if an unknown amount of air was disposed in the front of the nozzle. This also permits pressure to be precisely predetermined, again, which would not be possible if an undetermined amount of air was disposed in the front of the nozzle.

This step of insertion of the cartridge/nozzle assembly 10 into injector 32 is typically performed immediately prior to injection. Thus, with assembly 10 in place, the needleless injector 32 can be activated, forcing ram 44 and plunger 24 forwardly, thereby driving injectate through slots 56 in outlet valve 46, around body 58 disposed within recessed portion 50, through valve channels 64 and into aperture channel 54 and aperture 52 and into the patient. Because of the configuration of outlet valve 46, throat 21 and the inner walls of recessed portion 50, there is very little pressure drop as fluid is being forced out of the cartridge and out of injection aperture 52.

Embodiment of FIGS. 11, 12A and 12B

FIGS. 11, 12A and 12B depict an alternate embodiment of the prefilled cartridge/nozzle assembly, indicated generally at 110. In place of an outlet valve, embodiment 110 includes an elastomeric membrane 166 which is designed to burst open when a predetermined pressure has been applied, as shown in FIGS. 12A and 12B. Membrane 166 normally has a weakened portion along which the break will occur. In the depicted embodiment this weakened portion takes the form of a notch 167 which extends most but not all of the 360° around the inner throat 121 of cartridge 112. Membrane 166 is typically held in place by an aluminum seal 168 which is often used to help seal medication-containing cartridges.

In other respects embodiment 110 is much like embodiment 10 in that it includes O-rings 122 and nozzle 114, and is typically prefilled with injectate. Membrane 166 is designed to burst open when it is loaded into a needleless injector system as the plunger (not shown) is slightly depressed by the injector ram (not shown) as explained earlier. Upon bursting of membrane 166, injectate flows into the recess 155 in the forward end of the nozzle 114, thereby displacing any air and preparing the assembly for an injection.

Embodiment of FIGS. 13A and 13B

FIGS. 13A and 13B depict another alternate embodiment of the cartridge/nozzle assembly, indicated generally at 210. This embodiment utilizes an aluminum seal 268 like embodiment 110, but also includes an outlet valve 246. Outlet valve 246 includes a pair of radially extending wings 270 which are clamped under aluminum seal 268 until a predetermined amount of pressure forces outlet valve 246 out of the inner throat 221 of cartridge 212. When this predetermined pressure is reached, wings 270 pull out from seal 268 and the valve shifts forwardly into the recessed portion 250 of nozzle 214 until it comes into contact with the nozzle abutment surface 248.

Other than the presence of wings 270, outlet valve 246 is the same as the previously described outlet valve 46 in the cartridge/nozzle assembly 10 of FIGS. 1–10. Thus, when outlet valve 246 is shifted to its forward position depicted in FIG. 13B, injectate is permitted to flow out of cartridge 212 and into recessed portion 250 to displace any air and thus prepare the assembly 210 for an injection, as described above.

Figure 14A:
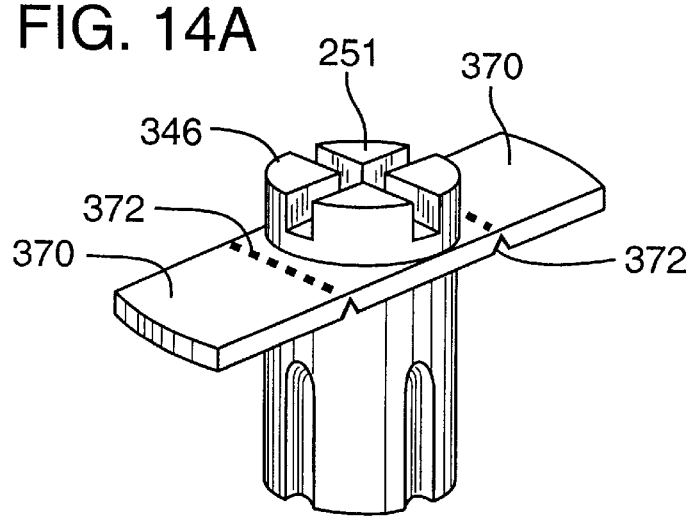
FIG. 14A is an isometric view of an outlet valve corresponding to the outlet valve depicted in FIGS. 13A and B except that the valve wings are notched to facilitate tearing when pressure is exerted on the valve.
Figure 14B:
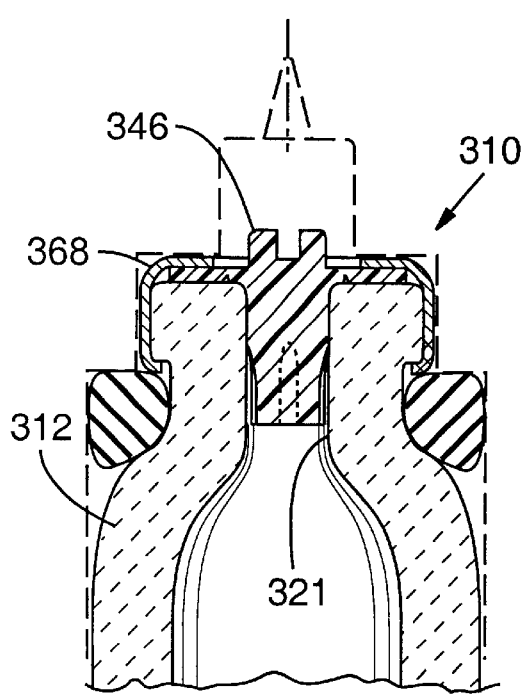
FIG. 14B is a view corresponding to FIG. 13A except that the notched-wing version of the outlet valve, shown in FIG. 14A, is depicted.
Figure 14C:
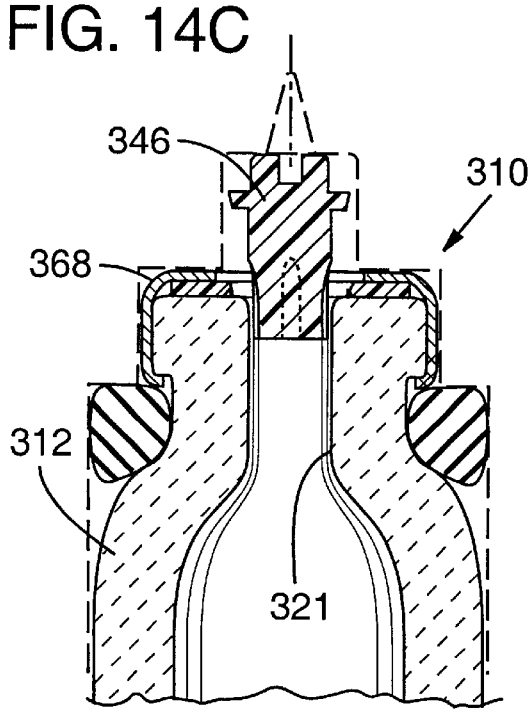
FIG. 14C corresponds to FIG. 14B except that the outlet valve is shown in its open position.

Embodiment of FIGS. 14A–C

The cartridge/nozzle assembly 310 of FIGS. 14A–C is identical to assembly 210 except that wings 370 of outlet valve 346 include weakened portions. In the depicted embodiment these weakened portions take the form of a pair of notches 372. Thus, when the cartridge/nozzle assembly 310 is mounted into a needleless injection system (not shown), instead of wings 370 pulling out of engagement with seal 368, the wings typically tear at notches 372 to permit outlet valve 346 to shift to the forward position depicted in FIG. 14C. In other respects the operation of cartridge/nozzle assembly 310 is the same as assemblies 10 and 210 described above.

Figure 15:
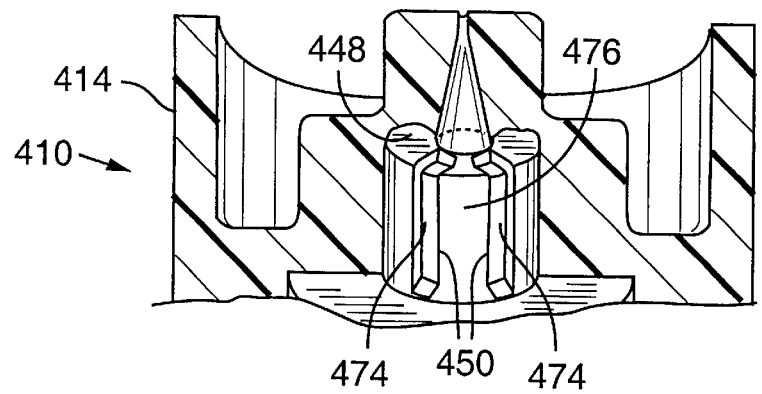
FIG. 15 is a fragmentary side elevation sectional view of yet another alternate embodiment of the nozzle without the cartridge or the outlet valve, showing ribs in the nozzle recess.
Figure 16A:
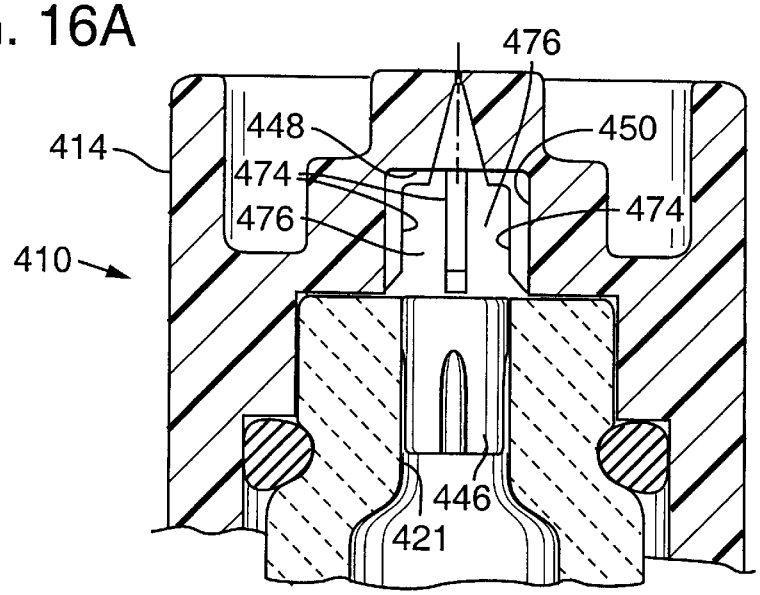
FIG. 16A is an enlarged side elevation sectional view of the embodiment of FIG. 15, showing the cartridge and the outlet valve in its closed position.
Figure 16B:
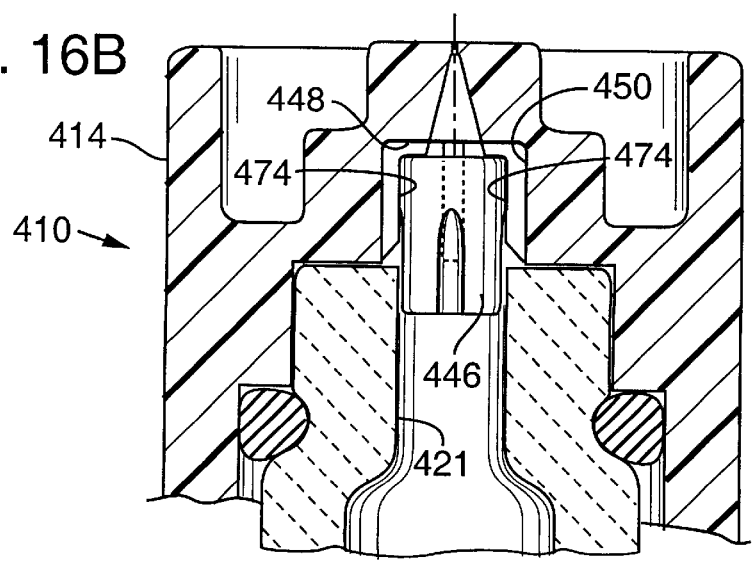
FIG. 16B is a view corresponding to FIG. 16A except that the outlet valve is shown in its forward position.

Embodiment of FIGS. 15, 16A and 16B

The cartridge/nozzle assembly 410 of FIGS. 15, 16A and 16B is identical to assembly 10 in FIGS. 1–10 except that recessed portion 450 of nozzle 414 includes a plurality of evenly spaced ribs 474. In the depicted embodiment four such ribs 474 are included. They are sized such that outlet valve 446 fits snugly into recessed portion 450 as shown in FIG. 16B. Channels 476 defined between ribs 474 permit fluid to flow around outlet valve 446 to orifice 52. In other respects cartridge/nozzle assembly 410 is constructed and operates in the same manner as assembly 10 of FIGS. 1–10.

Figure 17A:
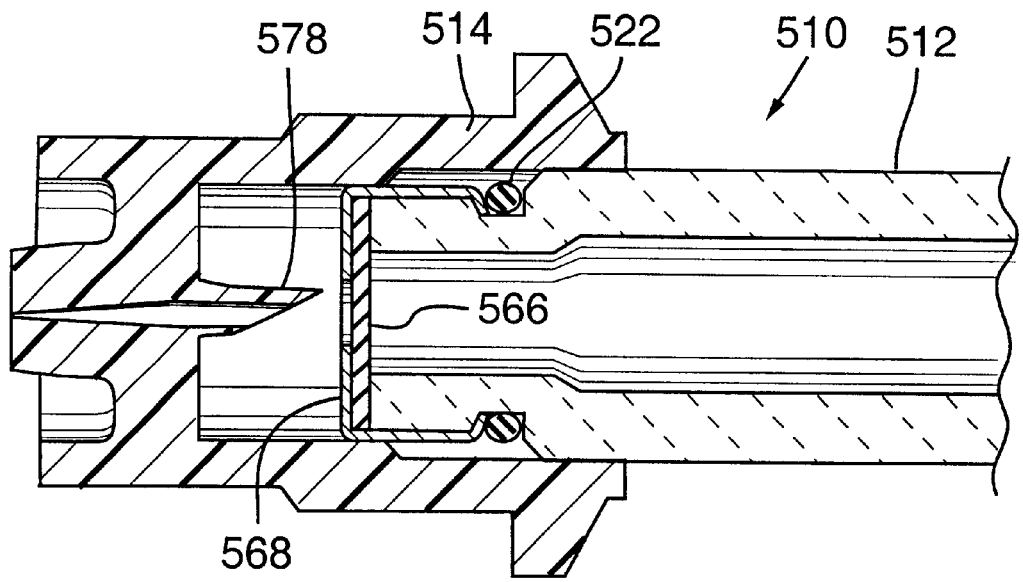
FIG. 17A is a side elevation view of an alternate embodiment of the invention.

The Embodiment of FIGS. 17A and B

Figure 17B:
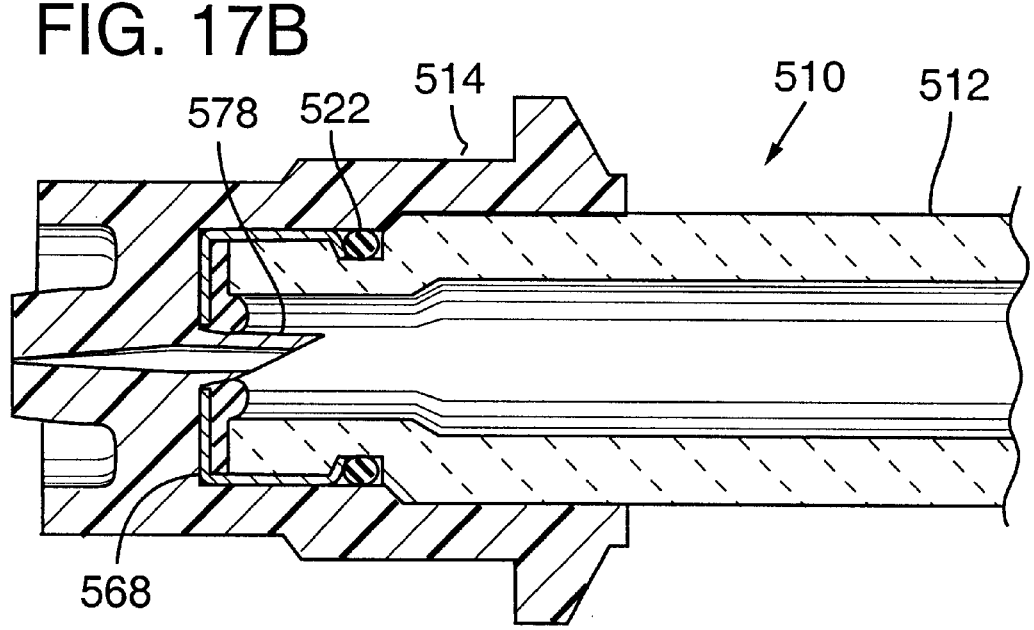
FIG. 17B is a view which corresponds to that of 17A.

FIGS. 17A and B depict another alternate embodiment of the cartridge/nozzle assembly shown generally at 510. The assembly includes a cartridge 512 and a nozzle 514. Cartridge 512 is prefilled with injectate as described above and is sealed with an aluminum seal 568 and an elastomeric membrane 566. A spoke 578 is provided to pierce membrane 566 when the cartridge is inserted all of the way into position in the nozzle, as shown in FIG. 17B. This is typically done shortly prior to injection. A plastic spike seal 580 is provided adjacent the spike to prevent leakage of injectate. The assembly 510 is then mounted into a needleless injector system such as described above, with the air being displaced to prepare the unit for injection.

In other respects, cartridge/nozzle assembly is the same in structure and operation as the previously described embodiments.

The Embodiment of FIGS. 18–22

Figure 18:
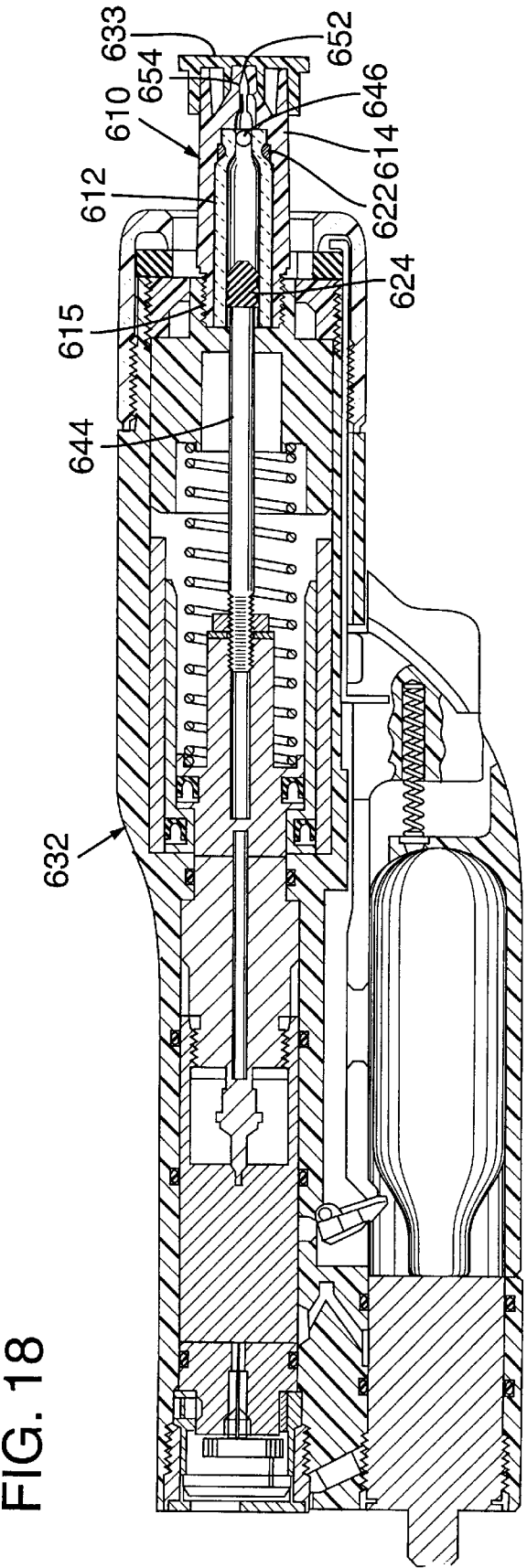
FIG. 18 is a side elevation sectional view showing the position of the cartridge and nozzle with an alternate embodiment as depicted in FIGS. 19–22.

FIGS. 18–22 depict another alternate embodiment of the cartridge/nozzle assembly. The assembly, shown generally at 610, includes a cartridge 612 and a nozzle 614. FIG. 18 shows assembly 610 being threaded into a needleless injector 632. Injector 632 is the same as the previously-described injector 32, except for this threaded mounting. An anti-contamination cap 633 is also shown in FIG. 18. This cap is positioned over the forward end of nozzle 614 prior to use in order to prevent any contamination of the nozzle orifice 652 and of the injectate contained in the cartridge/nozzle assembly 610.

The depicted anti-contamination cap 633 is shown to be air tight. It should, however, be understood that the cap 633 will permit air and/or injectate to leak out of the nozzle orifice 652 when fluid pressure is exerted. Thus, as will be explained below, when the cartridge/nozzle assembly is mounted onto an injector 632, air and some injectate will leak past the cap 633. Alternatively the anti-contamination cap may include ribs (not shown) which permit the cap to be securely mounted to the forward end of nozzle 614 but which facilitate venting of air and injectate out of the nozzle during the installation process.

The cartridge 612 is normally formed of strengthened glass and is prefilled with liquid injectate. The depicted nozzle 614 is fabricated of high strength thermoplastic, typically polycarbonate. The cartridge 612 includes outer walls 618 which taper slightly at 620 at the forward portion thereof. Tapered walls 620 converge to form an inner throat 621 disposed at the forward end of the cartridge 612. An O-ring seal 622 is disposed adjacent this forward, tapered portion of cartridge 612 between the cartridge and the inner surfaces of the nozzle side walls 630. Another way to describe the positioning of the O-ring 622 is that it is disposed between an outwardly-facing surface of the cartridge (outer walls 618) and an inwardly facing surface of the nozzle, adjacent the rearward end of the throat. In the depicted embodiment a step 628 is shown in the inner surface of side walls 630 to provide a stop and a sealing surface for O-ring 622. Thus, when the cartridge is in place within the nozzle, the O-ring 622 prevents or at least reduces the flow of injectate along the interface between the outer surface of cartridge walls 618 and the inner surface of nozzle side walls 630, and maintains the high pressures required for proper needleless injections.

Figure 19:
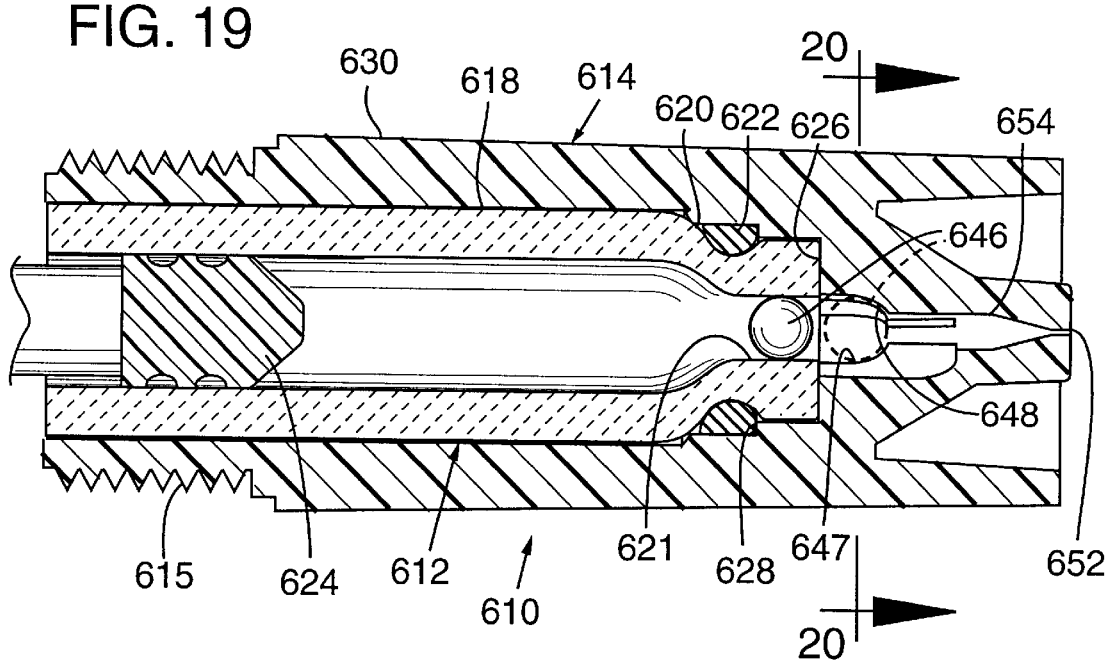
FIG. 19 is a side elevation sectional view of the embodiment of FIG. 18, with the plunger in its rearward position prior to installation of the assembly into an injector.
Figure 20:
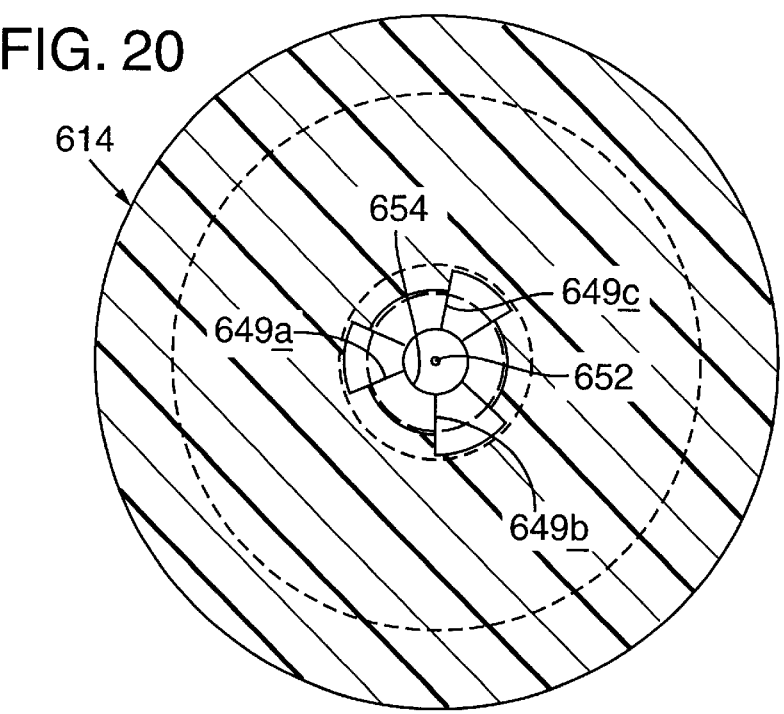
FIG. 20 is an end elevation sectional view taken along line 20—20 of FIG. 19.
Figure 21:
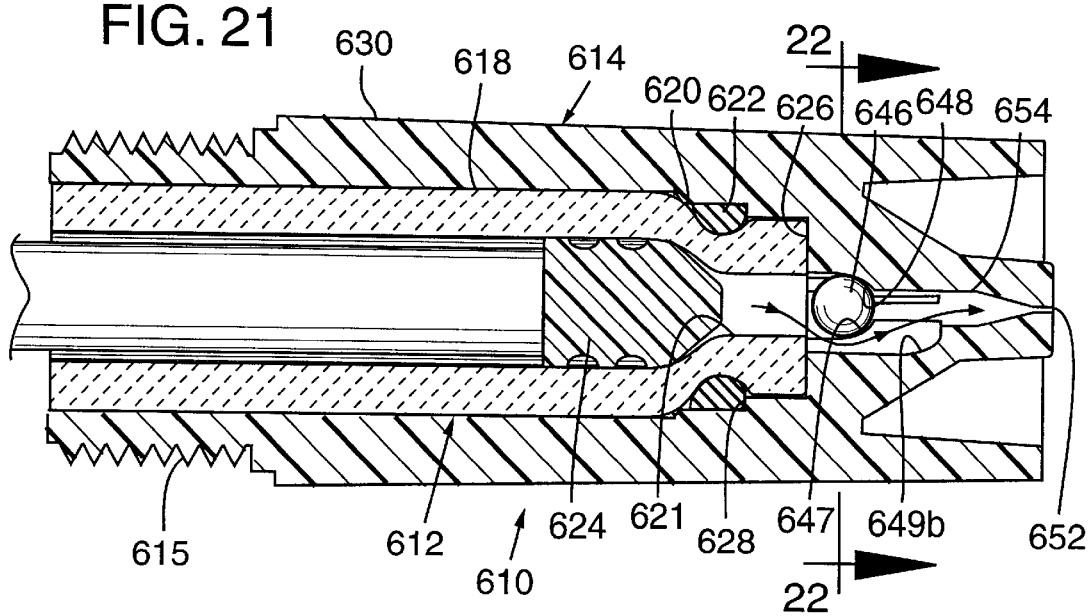
FIG. 21 is a side elevation sectional view of the embodiment of FIG. 18, except that the plunger is shown in its forward position after injectate has been injected from the assembly.
Figure 22:
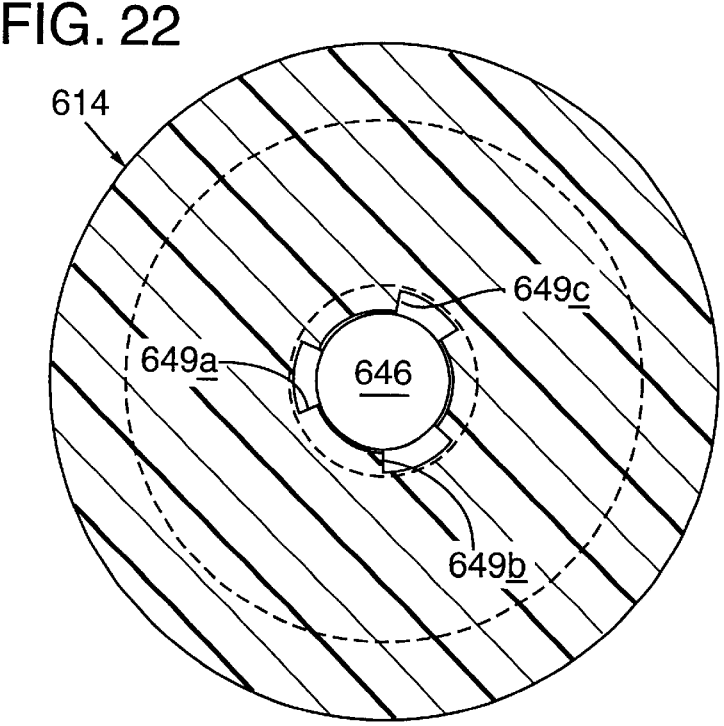
FIG. 22 is an end elevation sectional view taken along line 22—22 of FIG. 21.

A plunger 624 is disposed within the walls 618 of cartridge 612, and controls the flow of injectate out of the cartridge, as desired by the operator. At the factory, where the drug is filled aseptically (in a sterilized environment), the cartridge 612 is inserted into the nozzle 614 as shown in FIG. 19, and is then pressed forwardly and entirely into the nozzle until the forward end of the cartridge 612 abuts a cartridge abutment face 626 in the forward end of nozzle 614. This cartridge abutment face 626 will sometimes be referred to herein as a laterally extending interface surface.

As shown best in FIG. 19, an outlet valve 646 is initially disposed within the throat 621 adjacent the forward end of the cartridge 612. In the depicted embodiment the outlet valve 646 is spherical in configuration, and is fabricated of PTFE (polytetrafluoroethylene) or other resilient material which is suitable for drug storage and is capable of being sterilized prior to insertion into cartridge 612. As shown in FIG. 19, outlet valve 646 is designed to fit tightly within the forward end of cartridge 612. Because the valve 646 is spherical in configuration and in the preferred embodiment does not include any slots or apertures therein, and is sized such that it fits snugly within the throat 621 of cartridge 612, it might be said to include a body portion which fits against the walls of the cartridge throat 621 to prevent flow of injectate out of the cartridge until valve 646 is pushed out of the cartridge throat.

In the preferred embodiment, the diameter of outlet valve 646 is 0.110 inch, with the inner diameter of the throat 621 being 0.098 inch. This difference in sizing, along with the somewhat elastic properties of PTFE or other material from which outlet valve 646 is formed, permits a friction fit on the front end of the cartridge 612. In fact, outlet valve 646 would take a more oblong configuration than that shown in FIGS. 18 and 19, given the fact that the inner diameter of throat 621 is less than the diameter of outlet valve 646. Once hydraulic pressure is exerted on outlet valve 646, outlet valve 646 is forced out of the cartridge throat 621 into a valve receiving cup 647 and forwardly against a valve abutment surface 648 at the forward end of the valve-receiving cup, in the forward portion of nozzle 614. This typically happens when assembly 614 is threaded into the receiving thread of injector 632. This threading step results in plunger 624 being pushed slightly in an outward or forward direction (to the right in FIG. 18), thus pushing outlet valve 646 from throat 621 in a forward direction as well. The forward end of valve-receiving cup 647 terminates in a jet orifice 652 having a generally conical-shape nozzle orifice channel 654. The valve-receiving cup 647 will sometimes be referred to herein as a recessed portion of the nozzle.

To facilitate the flow of injectate from the cartridge 612 through the jet orifice 652, a plurality of bypass channels 649a, b and c are formed in the valve-receiving cup 647 and the valve abutment surface 648. They are of sufficient size that when the outlet valve 646 is disposed anywhere within the valve-receiving cup 647 or is disposed against the valve abutment surface 648, sufficient clearance is provided between the valve and the channels that injectate can bypass through the channels, into the orifice channel 654 and out the jet orifice 652. In the preferred embodiment where in the diameter of the outlet valve 646 is 0.110 inch, the valve-receiving cup is typically 0.115 inch in diameter, with the valve channels being 0.150 inch if they were measured in diameter, or 0.075 inch from the center of the valve-receiving cup to the edge of the channel. Using a configuration with three bypass channels 649a, b, c, each of the channels is typically 45° in width, and the channels are evenly spaced, here 120° degrees from each center line. Of course, it is possible that other channel configurations may be utilized, or other configurations may be substituted which permit flow of fluid past an outlet valve and into the orifice channel.

As the plunger 624 is pushed slightly in a forward direction, the pressure of the injectate fluid in cartridge 612 pushes outlet valve 624 from the throat 621 into the valve-receiving cup 647 and against valve abatement surface 648. Injectate fluid thus fills the valve-receiving cup 647 and the channels 649a, 649b and 649c, the nozzle orifice channel 654 and will dribble out of the nozzle orifice 652. With anti-contamination cap 633 in place, this will cause injectate to leak out of the cap as the assembly 610 is threaded into place on the injector 632.

When the device is ready to be activated, anti-contamination cap 633 is removed and the injector 632 is discharged. This drives plunger 624 forwardly, driving injectate out of the orifice 652 and into the patient (not shown).

In other respects, the cartridge/nozzle assembly 610 is similar to that of the embodiment of FIGS. 1–10 described above.

Operation of the Embodiment of FIGS. 18–22

Cartridge 612 is inserted into nozzle 614 at a factory location where aseptic conditions are assured. In such installation procedure the cartridge 612 is pressed forwardly and entirely into the nozzle until the forward end of the cartridge contacts cartridge abutment face 626 in the forward end of the nozzle. This position is depicted in FIG. 19. Because injectate is maintained within the glass cartridge, the assembly may be stored for extended periods prior to use. It is typically stored in a sterile pouch or bag (not shown). Many such stored cartridge/nozzle assemblies 610 may be provided to the patient. In this condition, the outlet valve 646 disposed within throat 621 seals the cartridge tight, preventing leakage of injectate out of the cartridge and preventing the injectate from being contaminated. Anti-contamination cap 633 (which is only shown in FIG. 18 after the assembly has been mounted onto an injector), assists in preventing contamination.

When the user is ready to administer the medication, assembly 610 is removed from its pouch or sterile bag and threaded into the front end of an injector, such as that shown in FIG. 18 at 632. As this threading is being done, plunger 624 is pushed forwardly because the injection ram 644 in the injector is stationary. This forces outlet valve 646 out of the cartridge throat 621 and into the valve-receiving cup 647 and against the valve abutment surface 648. Injectate thus fills all of the air spaces in the front of the nozzle, causing air and some injectate to leak out of the cap 633.

Once the cartridge/nozzle assembly 610 is in place, the device is ready for injection. Immediately prior to injection, anti-contamination cap 633 is removed from nozzle 614, the nozzle is placed against the skin of the patient, and the injector is activated.

In other respects, the operation of the cartridge/nozzle assembly 610 is essentially the same as that of assembly 10 depicted in FIGS. 1–20.

Changes and modifications of the present invention can be made without departing from the spirit and scope of the present invention. Such changes and modifications are intended to be covered by the following claims.

We claim:

1. A cartridge and nozzle assembly for use in a needleless injection system, comprising:
   a cartridge having a plunger disposed at a rearward end thereof, and including an inner portion with a throat at a forward portion thereof, the cartridge further including a generally laterally extending interface surface;
   a displaceable outlet valve initially disposed within the throat, the outlet valve having a channel-less valve body;
   a nozzle for receiving the cartridge, the nozzle defining a rearward, cartridge-receiving portion, and including a forward portion defining a valve-receiving portion with a plurality of channels and an injection orifice defined therein, the forward portion being configured to receive the valve when the valve is displaced to a forwardly disposed position, so that when the outlet valve is displaced from the throat into the valve-receiving portion of the nozzle, the inner portion of the cartridge has fluid access to the orifice via the channels, the nozzle further including a generally laterally extending interface surface which abuts the cartridge interface surface; and a seal disposed between the cartridge and the nozzle rearward of the interface surfaces for at least reducing leakage of injectate therebetween.

2. The assembly of claim 1 wherein the cartridge throat is tapered and the seal is mounted in a gap defined between the cartridge and the nozzle, adjacent to the cartridge throat.

3. The assembly of claim 1 wherein the valve-receiving portion of the nozzle is in the form of a recessed portion with a valve abutment surface having the channels defined therein.

4. The assembly of claim 3 wherein the channels include generally axially-extending portions in the recessed portion of the nozzle.

5. The assembly of claim 1 wherein the outlet valve has smooth and regular surfaces.

6. The assembly of claim 5 wherein the outlet valve is rounded.

7. The assembly of claim 6 wherein the outlet valve is generally spherical.

8. The assembly of claim 7 wherein the outlet valve is resilient.

9. The assembly of claim 8 wherein the cartridge is formed of glass.

10. A needleless injection apparatus, comprising:

a cartridge having a plunger disposed at a rearward end thereof, and including an inner portion with a throat at a forward portion thereof, a displaceable outlet valve initially disposed within the cartridge throat, the cartridge further including a generally outwardly facing surface;

a system for selectively providing driving force to drive the plunger in a forward direction;

a nozzle for receiving the cartridge, the nozzle defining a rearward, cartridge-receiving portion, and including a forward portion terminating in and defining a valve abutment surface having a plurality of channels and an injection orifice defined therein, the forward portion being configured to receive the valve when the valve is displaced to a forwardly disposed position such that the valve is disposed against the valve abutment surface, and so that the inner portion of the cartridge has fluid access to the orifice via the channels, the nozzle further including a generally inwardly facing surface which abuts the cartridge surface; and a seal disposed between the outwardly facing surface of the cartridge and the inwardly facing surface of the nozzle for at least reducing leakage of injectate therebetween.

11. The assembly of claim 10 wherein the valve abutment surface is cup-shaped.

12. The assembly of claim 11 wherein the outlet valve is rounded in at least the front end.

13. The assembly of claim 12 wherein the outlet valve is generally spherical.

14. The assembly of claim 1 wherein the outlet valve is resilient.

15. A method for preparing a needleless injection system, comprising:

selecting a glass cartridge with a plunger positionable at a rearward end and an inner portion with a throat at a forward portion, and an outlet valve positionable within the throat, the cartridge further including a generally laterally extending interface surface;

positioning a seal on the cartridge rearward of the laterally extending interface surface;

positioning one of the plunger or the outlet valve within the cartridge;

filling the cartridge with injectate prior to positioning the other of the plunger or the outlet valve in the cartridge;

positioning the other of the plunger or the outlet valve within the cartridge;

selecting a nozzle which includes a rearward, cartridge-receiving portion and a forward portion defining a valve-receiving portion with a plurality of channels and an injection orifice defined therein, the forward portion being configured to receive the valve when the valve is displaced to a forwardly disposed position, the nozzle further including a generally laterally extending interface surface; and installing the cartridge into the nozzle to form a cartridge/seal assembly such that the interface surfaces are in abutment and the seal is disposed rearwardly of such abutment.

16. The method of claim 15, further comprising positioning an anti-contamination cap on the front of the nozzle.

17. The method of claim 15, further comprising mounting the cartridge/nozzle assembly to the front end of an injector by exerting rearward pressure on the assembly such that an injector ram exerts forward pressure on the plunger, causing the outlet valve to be displaced from the throat and into the valve-receiving portion and resulting in the injectate displacing air in the forward portion of the nozzle.

18. The method of claim 17, further comprising effecting injection by activating the injector, causing the injector ram to push forwardly on the plunger, thereby causing injectate to be driven out of the nozzle orifice.

* * * * *